US007182948B2

(12) United States Patent
Tyndall et al.

(10) Patent No.: US 7,182,948 B2
(45) Date of Patent: Feb. 27, 2007

(54) TOPICAL VETERINARY COMPOSITIONS AND METHODS FOR THE TREATMENT AND PREVENTION OF INFECTION

(75) Inventors: Michael S. Tyndall, Springfield, MO (US); John M. Cunningham, Rogersville, MO (US); Michael D. White, Ozark, MO (US)

(73) Assignee: KO Manufacturing, Inc., Springfield, MO (US)

( * ) Notice: Subject to any disclaimer, the term of this patent is extended or adjusted under 35 U.S.C. 154(b) by 162 days.

(21) Appl. No.: 10/633,945

(22) Filed: Aug. 4, 2003

(65) Prior Publication Data

US 2005/0031705 A1 Feb. 10, 2005

(51) Int. Cl.
*A61K 45/00* (2006.01)
*A61K 47/00* (2006.01)
*A61K 39/00* (2006.01)
*A01N 39/00* (2006.01)
*A01N 59/00* (2006.01)

(52) U.S. Cl. .............................. 424/278.1; 424/184.1; 424/616; 424/600; 514/5

(58) Field of Classification Search ............ 424/184.1, 424/278.1, 616, 600; 514/5
See application file for complete search history.

(56) References Cited

U.S. PATENT DOCUMENTS

| | | | |
|---|---|---|---|
| 5,236,703 A | 8/1993 | Usala | |
| 5,824,359 A * | 10/1998 | Khan et al. ............... | 427/2.3 |
| 6,022,551 A * | 2/2000 | Jampani et al. ........... | 424/405 |
| 6,110,908 A | 8/2000 | Guthery | |
| 6,149,924 A | 11/2000 | Paul | |
| 6,248,343 B1 * | 6/2001 | Jampani et al. ........... | 424/405 |
| 6,258,368 B1 * | 7/2001 | Beerse et al. ............. | 424/404 |
| 6,436,445 B1 * | 8/2002 | Hei et al. .................. | 424/667 |
| 6,525,071 B2 * | 2/2003 | Dyer .......................... | 514/320 |
| 6,881,427 B2 * | 4/2005 | Mayne et al. .............. | 424/757 |
| 2002/0051789 A1 | 5/2002 | Wagter-Lesperance et al. | |
| 2002/0086039 A1 * | 7/2002 | Lee et al. .................. | 424/401 |
| 2003/0031727 A1 * | 2/2003 | Hahn et al. ................ | 424/617 |
| 2003/0077307 A1 | 4/2003 | Klofta et al. | |
| 2003/0114400 A1 | 6/2003 | Bennett et al. | |
| 2004/0102429 A1 * | 5/2004 | Modak et al. .............. | 514/184 |
| 2005/0015854 A1 * | 1/2005 | Eisenberg ................... | 2/409 |

FOREIGN PATENT DOCUMENTS

WO WO 01/41727 A1 * 6/2001

OTHER PUBLICATIONS (Uses of Iodine, http://www.pleasantridge.k12.ca.us/magnolia/elements/iodine/iodine2.html).*
(Rabies, Medicine Consumer Health, 2003; pp. 1-8, eMedicine.com).*
Jansen et al, Review Article, Bovine Encephalopathy and foot-and-mouth disease . . . , CEJOEM, 2001; 7(3-4): 155-67.*
OneLook definition: Iodophor.*
Harmon et al (Controlling Contagious Mastitis, 1996, http://www.nmconline.org/articles/contagious.htm. pp. 1-8).*
Abughazaleh, A.A., et al., Milk Conjugated Linoleic Acid Response to Fish Oil Supplementation of Diets Differing in Fatty Acid Profiles, J. Dairy Sci., 2003, pp. 944-953, vol. 86, No. 3.
Bitman, J., et al., Lipid Composition of Teat Canal Keratin Collected Before and After Milking from Holstein and Jersey Cows, J. Dairy Sci., 1991, pp. 414-420, vol. 74, No. 2.
Campbell, W., et al., The Impact of Fortification with Conjugated Linoleic Acid (CLA) on the Quality of Fluid Milk, J. Dairy Sci., 2003, pp. 43-51, vol. 86, No. 1.
Childs, G.V., Membrane Structure and Function, Internet Article: http://cellbio.utmb.edu/cellbio/membrane_intro.htm, 2001, 10 pp.
Chouinard, P.Y., et al., Milk Yield and Composition During Abomasal Infusion of Conjugated Linoleic Acids in Dairy Cows, J. Dairy Sci., 1999, pp. 2737-2745, vol. 82, No. 12.
Crist, W.L., et al., Mastitis and Its Control, University of Kentucky Extension Service—College of Agriculture, 1997, pp. 1-13.
Gaynor, P.J., et al., Milk Fat Yield and Composition During Abomasal Infusion of *Cis* or *Trans* Octadecenoates in Holstein Cows, J. Dairy Sci., 1994, pp. 157-165, vol. 77, No. 1.
Loor, J.J., et al., Reduced Fatty Acid Synthesis and Desaturation Due to Exogenous *trans*10, *cis*12-CLA in Cows Fed Oleic or Linoleic Oil, J. Dairy Sci., 2003, pp. 1354-1369, vol. 86, No. 4.
Mein, G.A., et al., Evaluation of Bovine Teat Condition in Commercial Dairy Herds: 1. Non-Infectious Factors, 2nd International Symposium on Mastitis and Milk Quality, Vancouver, Canada, 2001, pp. 347-351.
Neijenhuis, F., et al., Relationship Between Teat-End Callosity and Occurrence of Clinical Mastitis, J. Dairy Sci., 2001, pp. 2664-2671, vol. 84, No. 12.
Nickerson, S.C., et al, Effect of Postmilking Teat Antisepsis on Teat Canal Infections in Lactating Dairy Cows, J. Dairy Sci., 1990, pp. 373-380, vol. 73, No. 2.
Nickerson, S.C., Teat End Interactions with Germicides, Internet Article: http://www.nmconline.org/articles/teatend.htm, 2001.
Pankey, J.W.. et al., Evaluation of Nine Teat Dip Formulations Under Experimental Challenge, J. Dairy Sci., 1983, pp. 161-167, vol. 66, No. 1.

(Continued)

*Primary Examiner*—Robert A. Zeman
*Assistant Examiner*—Lakia J. Tongue
(74) *Attorney, Agent, or Firm*—Senniger Powers

(57) ABSTRACT

The present invention provides compositions and methods for the treatment of infection in a subject. More particularly, the invention provides a therapy for the treatment or prevention of mammary infections, such as bovine mastitis, comprising the topical administration to a subject of an anti-microbial agent and a phospholipid-containing skin conditioner.

35 Claims, No Drawings

OTHER PUBLICATIONS

Perfield II, J.W., et al., Effects of Dietary Supplementation of Rumen-Protected Conjugated Linoleic Acid in Dairy Cows during Established Lactation, J.Dairy Sci., 2002, pp. 2609-2617, vol. 85, No. 10.

Peterson, D.G., et al., Analysis of Variation in *cis*-9, *trans*-11 Conjugated Linoleic Acid (CLA) in Milk Fat of Diary Cows, J. Dairy Sci., 2002, pp. 2164-2172, vol. 85, No. 9.

Sordillo, L.M., et al., Symposium: Bovine Immunology—Immunobiology of the Mammary Gland, J. Dairy Sci., 1997, pp. 1851-1865, vol. 80, No. 8.

Lipid Stucture and Function, Natural Toxins Research Center at Texas A&M University-Kingsville, Internet Article: http://ntri.tamuk.edu/cell/lipid.html, date unknown, 6 pp.

Membrane Structure and Function, Natural Toxins Research Center at Texas A&M University-Kingsville, Internet Article: http://ntri.tamuk.edu/cell/membranes.html , date unknown, 8 pp.

Summary of Peer-Reviewed Publications of Efficacy of Premilking and Postmilking Teat Disinfectants Published Since 1980, National Mastitis Council, Jan. 2003.

International Preliminary Examination Report for PCT/US03/283, dated Jul. 28, 2005.

* cited by examiner

TOPICAL VETERINARY COMPOSITIONS AND METHODS FOR THE TREATMENT AND PREVENTION OF INFECTION

FIELD OF THE INVENTION

The present invention provides compositions and methods for the treatment and prevention of infection. The invention is directed toward a therapy for the treatment or prevention of mammary infections, such as bovine mastitis, comprising the administration to a subject of a topical veterinary composition comprising an anti-microbial agent and a skin conditioner.

BACKGROUND OF THE INVENTION

The spread of bacterial infection in connection with cow teats during the milking process results in the spread of the infectious mammary disease known as mastitis. Bovine mastitis is an inflammation of the udder. The characteristic features of inflammation are swelling, heat, redness, pain, and disturbed function. This condition, which is almost exclusively initiated by pathogenic microorganisms that have entered the teat canal after the milking process, occludes milk flow and production, decreases milk value, and may permanently impair an animal's ability to produce milk. More than 80 species of microorganisms have been identified as causal agents, although approximately 95% of mastitis is believed to be caused by four pathogens: staphylococcus aureus, streptococcus agalactiae, streptococcus dysagalactiae, and streptococcus uberis. Mastitis-causing pathogens fall into two categories, namely, contagious and environmental. Contagious bacteria, such as streptococcus agalactiae and staphylococcus aureus, primarily colonize host tissue sites such as mammary glands, teat canals, and teat skin lesions; and are spread from one infected cow to another during the milking process. Environmental bacteria, often streptococci, enterococci, and coliform organisms, are commonly present within the cow's surroundings from sources such as cow feces, soil, plant material, bedding, or water; and infect by casual opportunistic contact with an animal.

The distinction between contagious and environmental pathogens, although not exclusive, is of practical importance because different dairy herd maintenance measures are needed for the different groups of microorganisms. In all bovine mastitis cases, whatever the causal microorganism, the route of transmission of the invading pathogen into the inner gland of the udder is through the teat orifice and teat canal. The common sources of harmful microorganisms include unsanitary milking equipment, the milker, other mastitic animals, an unsanitary stable environment, and the animals' own elimination (defecation/urination) processes.

A 1996 study by the National Mastitis Council (NMC) estimated annual monetary losses per cow due to mastitis at $184.40 totaling to an extrapolated average of $1.7 billion in the U.S. alone (Crist, W. L. et al., (1997) Mastitis and Its Control, University of Kentucky Extension Service—College of Agriculture). The spread of this disease is generally reduced by the use of antimicrobial compositions; for example, antimicrobial teat dips containing iodine have been shown to be effective against mammary infections and mastitis-causing bacteria (Pankey, J. W. et al., (1983) J. Dairy Sci. 66 (1), 161–167). These compositions are usually administered to the teat by dipping or spraying the teat prior to milking as well as after removal of the milking cup. To reduce mastitis, commercial teat dips have been developed containing a variety of antimicrobial agents including iodophors, quaternary ammonium compounds, chlorine release compounds (e.g. alkali hypochlorites), oxidizing compounds (e.g. hydrogen peroxide, peracids), protonated carboxylic acids (e.g. heptanoic, octanoic, nonanoic, decanoic, undecanoic acids), acid anionics (e.g. alkylaryl sulfonic acids), chlorine dioxide (from chlorite), and bisbiguanides such as chlorhexidine. These agents, which have varying degrees of effectiveness, limit the transmission of mastitis by reducing pathogen populations on the teat. However, there are problems associated with the use of antimicrobials. The most prevalent are irritation to the teat and teat cracking. To alleviate these problems, emollient additives such as glycerin and lanolin have been included in such compositions. However, even with the use of these emollients skin irritation can still occur.

The NMC not only stresses the importance of proper teat sanitation, but also proper teat care for the prevention of mastitis. The economic harm caused by mastitis has led to much research in its control. Physical stresses as well as environmental conditions have been reported to be large contributors to mastitis infection (See U.S. Patent: 20020051789). Since it was documented that sub-clinical mastitis was directly related to poor teat condition (Neijenhuis, P. et al., (2001) J. Dairy Sci. (84) 2664–2672), a number of commercial teat dip solutions incorporating conditioning agents have evolved (National Mastitis Council, Summary of Peer-Reviewed Publications on Efficacy of Premilking and Postmilking Teat Disinfectants Published Since 1980; January 2002). Recently, teat end callosity and roughness have been shown to have a direct relationship with clinical mastitis (Neijenhuis, F. et al., (2001) J. Dairy Sci. (84) 2664–2672). The reduction of chapping and irritation of teats as well as keeping the teat flexible is very important in controlling mammary infections. Currently, glycerin is often used as a teat conditioner in teat dip solutions. However, studies indicate no significant decrease in mastitis-causing bacteria such as staphylococcus aureus, streptococcus agalactiae, or coliforms when the glycerin content is increased from 2% to 10% in a 1% iodine teat dip solution (National Mastitis Council, Summary of Peer-Reviewed Publications on Efficacy of Premilking and Postmilking Teat Disinfectants Published Since 1980; January 2002).

Thus, although many teat dip products are available, there is a continuing need for new and effective teat dip compositions having immediate and long lasting antimicrobial effect against a wide spectrum of mastitis-causing organisms that also aid in overall skin condition of the teat.

SUMMARY OF THE INVENTION

Among the several aspects of the present invention is to provide a method and a composition for the treatment and prevention of mammary infections in a subject. The composition comprises an anti-microbial agent and a phospholipid-containing skin conditioner, and the method comprises administering to a subject a topical veterinary composition comprising an anti-microbial agent and a phospholipid-containing skin conditioner.

Another aspect of the invention is to provide such compositions and methods that do not chap, peel, or irritate the subject's skin.

In one embodiment, the composition comprises the anti-microbial agent iodine, and a phospholipid-containing skin conditioner, wherein the phospholipid is selected from the group consisting of: linoleamidopropyl phosphatidylglycerol dimonium chloride phosphate, cocoamidopropyl phosphatidylglycerol dimonium chloride phosphate, sunfloweramidopropyl phosphatidylglycerol dimonium chloride phosphate, sodium olivamidopropyl phosphatidylglycerol dimonium chloride phosphate, stearamidopropyl phosphatidylglyoerol dimonium chloride phosphate, ricinoleamidopropyl phosphatidylglycerol dimonium chloride phosphate, di-linoleamidopropyl phosphatidylglycerol dimonium chloride phosphate, poly (ethylene glycol)$_{n=8}$ dimethicone sunfloweramidopropyl phosphatidylglycerol dimonium chloride phosphate complex, dimethicone saffloweramidopropyl phosphatidylglycerol dimonium chloride phosphate complex, sodium grapeseedamidopropyl phosphatidylglycerol dimonium chloride phosphate, and sodium borageamidopropyl phosphatidylglycerol dimonium chloride phosphate.

Other aspects of the invention are described in more detail below.

Abbreviations and Definitions

Where used, either alone or within other terms such as "haloalkyl," "alkylsulfonyl," "alkoxyalkyl," and "hydroxyalkyl," the term "alkyl" is a linear, cyclic, or branched radical having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl, and the like.

The term "alkylamino" is an amino group that has been substituted with one or two alkyl radicals. Preferred are "lower N-alkylamino" radicals having alkyl portions having 1 to 6 carbon atoms. Suitable lower alkylamino may be mono or dialkylamino such as N-methylamino, N-ethylamino, N,N-dimethylamino, N,N-diethylamino, or the like.

The term "aryl," alone or in combination, is a carbocyclic aromatic system containing one, two, or three rings wherein such rings may be attached together in a pendent manner or may be fused. The term "aryl" includes aromatic radicals such as benzyl, phenyl, naphthyl, tetrahydronaphthyl, indane, and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl, and aralkoxycarbonyl.

When used in combination, for example "alkylaryl" or "arylalkyl," the individual terms listed above have the meaning indicated above.

The description "concentrate" is in reference to the phrase "teat sanitizer concentrate" in which the diluent of a ready-to-use teat sanitizer is removed during manufacture and diluent is re-added at the convenience of the user. In addition, it is not a requirement that the diluent re-added has to match the diluent removed—only a diluent compatible with the concentrated mixture is required.

The term "emollient" refers to an agent that softens or soothes the skin. Emollients typically act as a replenisher of oils and fats to the skin; but, an emollient may promote the retention of moisture in skin while achieving a softening or soothing effect.

The term "humectant" refers to a substance that promotes retention of moisture; and, in particular to this embodiment, the retention of moisture in skin. Humectants do not directly soften and soothe skin, but allow the skin to retain its natural moisture.

The term "subject" for purposes of treatment includes any lactating animal. The subject can be a domestic livestock species, a laboratory animal species, a zoo animal, or a companion animal. In one embodiment, the subject is a cow.

The phrase "therapeutically effective" is intended to qualify the amount of the topical veterinary composition comprising an antimicrobial agent and a phospholipid-containing skin conditioner, which will achieve the goal of improvement in disorder severity and the frequency of incidence over no treatment.

DESCRIPTION OF THE PREFERRED EMBODIMENTS

The present invention provides a therapy comprising the administration to a subject of a therapeutically effective amount of a topical veterinary composition comprising an anti-microbial agent and a phospholipid-containing skin conditioner. The therapy is used to treat or prevent infection, for example, mammary infections such as bovine mastitis.

Phospholipids

A number of suitable phospholipids may be employed in the composition of the current invention. Suitable phospholipids act as skin conditioners and prevent chapping, peeling, and irritation of the skin. In addition, suitable phospholipids will aid in the flexibility of the skin. In one embodiment, the composition contains, for example, the phospholipid cis-9, trans-11-octadecanamidopropyl phosphatidylglycerol phosphate, Formula I.

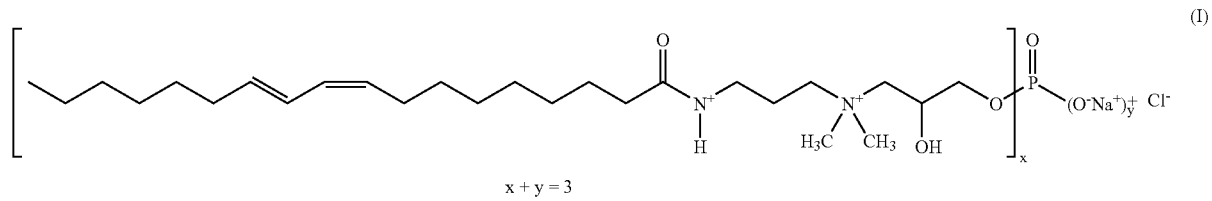

$x + y = 3$

Some phospholipids suitable for the present invention may be described as diesters or triester phosphatides consisting of a glycerol or triglyceride, one to three fatty acods or natural oils, and a hydrophilic phosphorylated group, and of the general structure: (fatty acid) hd 2—glycerol—phosphorylated group or (fatty acid)$_3$—triglyceride—phosphorylated group and their organosilicone modified counterparts. The fatty acid preferred is linoleic, an unsaturated fatty acid derived from safflower oil, but any unsaturated fatty acid such as lauroleic, myristoleic, linoleic, eleostearic, licanic, and arachadinic and their corresponding isomers or any natural oil such as coconut, olive, palm, or castor oil, or, any combination of a natural oil and an unsaturated fatty acid may be substituted. Synthetic phospholipid alternatives to the natural derived oils and fatty acids are commerocially abundant and do not interfere with the general function of the phospholipid.

In one embodiment, the ratio of phospholipid to antimicrobial agent is between about 0.1:1 and about 10:1. Unless otherwise stated, all ratios and percentages listed herein are by weight; and, unless otherwise stated, refer to ready-to-use compositions.

In a further embodiment, the ratio of phospholipid to antimicrobial agent is between about 1:1 and about 4:1.

In still further embodiment, the ratio of phospholipid to antimicrobial agent is between about 1.5:1 and about 2.5:1, between about 1.75:1 and about 2.25:1, or about 2:1.

As a general proposition, the phospholipid concentration is between about 0.01 and about 20 percent of the overall composition. In a preferred embodiment, phospholipid constitutes between about 0.9 and about 1.1 percent of the overall composition. In another preferred embodiment, the phospholipid constitutes between about 1.9 and 2.1 percent of the overall composition. In still a further preferred embodiment, the phospholipid constitutes between about 3.9 and 4.1 percent. The composition is provided as a ready-to-use formula having the foregoing phospholipid concentrations, or is provided as a concentrate to be diluted. When the composition is provided as a concentrate having a lesser concentration of the diluent than the ready-to-use formula, the phospholipid concentration is proportionally greater such that it provides the desired final concentration after being diluted by the user or supplier.

In another embodiment, compounds that are useful as a phospholipid in connection with the compositions and methods of the present invention, include, but are not limited to:

linoleamidopropyl phosphatidylglycerol dimonium chloride phosphate, marketed under the trade name Arasilk EFA and Colalipid SAFL;

cocoamidopropyl phosphatidylglycerol dimonium chloride phosphate, marketed under the trade name Arasilk CDM and Colalipid C;

sunfloweramidopropyl phosphatidylglycerol dimonium chloride phosphate, marketed under the trade name Colalipid SUN;

sodium olivamidopropyl phosphatidylglycerol dimonium chloride phosphate, marketed under the trade name Colalipid OL;

stearamidopropyl phosphatidylglycerol dimonium chloride phosphate, marketed under the trade name Arasilk SV and Colalipid ST;

ricinoleamidopropyl phosphatidylglycerol dimonium chloride phosphate, marketed under the trade name Colalipid RC;

di-linoleamidopropyl phosphatidylglycerol dimonium chloride phosphate, marketed under the trade name Colalipid DLO;

poly (ethylene glycol)$_{n=8}$ dimethicone sunfloweramidopropyl phosphatidylglycerol dimonium chloride phosphate complex, marketed under the trade name Colalipid SIL;

dimethicone saffloweramidopropyl phosphatidylglycerol dimonium chloride phosphate complex, marketed under the trade name Arasilk PLN;

sodium grapeseedamidopropyl phosphatidylglycerol dimonium chloride phosphate, marketed under the trade name Colalipid GS; and sodium borageamidopropyl phosphatidylglycerol dimonium chloride phosphate, marketed under the trade name Arasilk GLA.

Antimicrobial Agents

A number of suitable antimicrobial agents are employed in the compositions of the present invention. The criteria employed in selecting an antimicrobial agent include low skin irritancy, water solubility, and effectiveness against pathogens such as staphylococcus aureus, streptococcus agalactiae, streptococcus dysagalactiae, and streptococcus uberis. In one embodiment, the antimicrobial agent is iodine. In another embodiment, the antimicrobial agent is a quaternary ammonium compound. In yet another embodiment, the antimicrobial agent is a chlorine release compound such as alkali hypochlorite. In still another embodiment, the antimicrobial agent is hydrogen peroxide. In a further embodiment, the antimicrobial agent is a protonated carboxylic acid (e.g. heptanoic, octanoic, nonanoic, decanoic, undecanoic, capric, lauric, myristic, palmitic, stearic, oleic, linoleic, and linolenic acid and their corresponding isomers). In a still further embodiment, the antimicrobial agent is an alkylaryl sulfonic acid. In another embodiment, the antimicrobial agent is chlorine dioxide. In yet another embodiment, the antimicrobial agent is chlorhexidine.

As a general proposition, the concentration of the antimicrobial agent in the composition varies depending upon the specific agent selected. In one preferred embodiment the anti-microbial agent is iodine. In one embodiment the concentration of iodine is between about 0.1 and about 2.0 percent of the overall composition. When the composition is provided as a concentrate having a lesser concentration of the diluent than the ready-to-use formula, the iodine or other anti-microbial agent concentration is proportionally greater such that it provides the desired final concentration after being diluted by the user or supplier.

Other Agents

The compositions of the present invention are preferably prepared with the incorporation of a chemical agent or agents that have an emollient activity on the skin. Anhydrous oil systems and water-in-oil systems are not preferred in the present invention, due to the fact that residual oil can promote adhesion of waste particulate matter and compromise the antimicrobial effectiveness of the composition. Therefore, oil-in-water compositions are preferred in the present compositions. The preferred emollient system for the compositions of the present invention also includes a water-soluble refatting agent. One preferred emollient for the compositions of the present invention is a phospholipid in combination with glycerin. The total concentration of the emollient and re-fatting agents in the antimicrobial compositions is generally about 0 to about 25 percent (all percentages herein are by weight), more preferably about 2 to about 15 percent, and even more preferably about 4 to about 6 percent; and, increases proportionally when used in the form of a concentrate as the diluent is removed.

Other adjuvants, such as pH adjustors and buffering agents, can be blended with the compositions of the present invention. Useful pH adjustors can be either organic or inorganic acids or bases, alone or in combination with their respective salts. Preferred buffering agents include, for example, citric acid, sorbic acid, ascorbic acid, malic acid, and succinic acid. Preferred basifying agents include, for example, triethanolamine, ammonium hydroxide, potassium hydroxide, and sodium hydroxide. The pH adjustors, when present, are used in sufficient quantities to bring the pH of the composition into the desired range, generally from about pH 4 to about pH 6. Other adjuvants can include defoamers, such as dimethicone and dicyclomethicone; emollients, such as oleyl alcohol, oleyl lanolate, and lanolin; humectants such as propylene glycol and sorbitol; and nutrients, such as vitamin E (alpha tocopherol). In addition, optional ingredients may include both water and oil-soluble vitamins and wound-healing agents (e.g., proteins, lipids, nucleic acids, etcetera).

The compositions of the present invention can also optionally include stabilizers and thickening agents to achieve viscosities within a useful range appropriate for the mode of application. Such agents include hydroxypropyl methyl cellulose, hydroxypropyl cellulose, methyl cellulose, carboxy methyl cellulose, emulsifying waxes, alkyl triammonium methosulfate, and ceteraryl octanoate. When used, the total concentration of the stabilizers and thickening agents in compositions of the present invention are generally about 0 to about 2 percent, more preferably at least about 0.01 to about 0.75 percent, and even more preferably about 0.3 to about 0.6 percent. Formulations wherein the total concentration of the stabilizers and thickening agents is less than about 0.1 percent, and preferably not more than about 0.05 percent, can be utilized. When the composition is provided as a concentrate having a lesser concentration of the diluent than the ready-to-use formula, the stabilizer and thickening agent concentration is proportionally greater such that it provides the desired final concentration after being diluted by the user or supplier. Although the compositions are aqueous based, certain ingredients may require the presence of a more lipophilic solvent for proper stabilization. Preferred additional solvents are polyhydric alcohol solvents, or "polyol" solvents, such as the polyalkylene glycols having alkylene moieties containing about 2–3 carbon atoms, preferably the polyethylene glycols. Molecular weight ranges of from about 200–4000 are preferred for the polyalkylene glycols (e.g., propylene glycol). These polyol solvents are useful as a humectant and serve to help solubilize the lipophilic compounds.

Generally speaking, the compositions of the present invention are preferably administered to the subject immediately prior to the milking process as well as immediately after the completion of the milking process.

Field Studies

Tables T1–T5 depict results attained from various field studies as described below, wherein:

composition "A" is a commercially available teat dip that contains 0.5% iodine and 74% emollients;

composition "B" is a composition of the present invention comprising 0.5% iodine and 1.0% phospholipid and 0% added emollient;

composition "C" is a commercially available teat dip that contains 1.0% iodine and 10.0% emollients;

composition "D" is a composition of the present invention comprising 0.5% iodine and 1.0% phospholipid with 5% added emollient; and composition "E" is a composition of the present invention comprising 1.0% iodine and 1.0% phospholipid with 5% added emollient.

Table T1 lists the quantity and qualities of the milk obtained from a 30 day study of cows who have birthed once (primiparous) and those who have birthed more than once (multiparous) for a commercially available teat dip that contains 0.5% iodine with 74% emollients (A) and a composition of the present invention comprising 0.5% iodine and 1.0% phospholipid with 0% added emollient (B). The treatment P value indicates that the only statistical significance between the two products is the fat percent and MUN value.

TABLE T1

(Effect of teat dip on milk yield and composition)

| | Primi-parous | | Multiparous | | P value | | |
|---|---|---|---|---|---|---|---|
| Item[1] | A | B | A | B | Treatment | Parity | *Parity |
| N | 23 | 25 | 44 | 41 | | | |
| Milk, kg/day | 40.9 | 43.3 | 41.0 | 41.6 | 0.8970 | 0.1925 | 0.1683 |
| ECM, kg/day | 41.3 | 41.3 | 40.9 | 42.6 | 0.6759 | 0.5901 | 0.3028 |
| Fat, % | 3.64 | 3.46 | 3.40 | 3.53 | 0.0530 | 0.3207 | 0.0530 |
| Protein, % | 3.09 | 3.20 | 3.14 | 3.13 | 0.1490 | 0.6482 | 0.0018 |
| Lactose, % | 4.95 | 5.00 | 4.95 | 4.94 | 0.3224 | 0.0955 | 0.0730 |
| SNF, % | 8.97 | 9.17 | 8.99 | 9.02 | 0.6567 | 0.0352 | 0.0003 |
| MUN, mg/dL | 16.23 | 16.48 | 16.73 | 16.66 | 0.0278 | 0.0545 | 0.3713 |
| Fat, kg/day | 1.44 | 1.38 | 1.41 | 1.50 | 0.3319 | 0.3214 | 0.1081 |
| Protein, kg/day | 1.26 | 1.38 | 1.28 | 1.29 | 0.5450 | 0.1621 | 0.0071 |
| Lactose, kg/day | 2.03 | 2.17 | 2.04 | 2.06 | 0.6728 | 0.1245 | 0.0782 |

[1]Values have been adjusted for covariate

Table T2 scores the teat and teat-end condition following a 30 day study of primiparous and multiparous cows for a commercially available teat dip that contains 0.5% iodine and 74% emollients (A) and a composition of the present invention comprising 0.5% iodine and 1.0% phospholipid with 0% added emollient (B). The treatment P value indicates that there in no statistical significance between the two products.

TABLE T2

(Effect of teat dip on teat condition and teat ends)

| | Primiparous | | Multiparous | | P value | | |
|---|---|---|---|---|---|---|---|
| Item[1] | A | B | A | B | Treatment | Parity | *Parity |
| N | 21 | 26 | 45 | 46 | | | |
| Left front | 1.81 | 2.04 | 2.04 | 1.97 | 0.5125 | 0.5338 | 0.2297 |
| Right front | 1.73 | 2.07 | 1.93 | 1.91 | 0.1853 | 0.8715 | 0.1489 |
| Left rear | 1.39 | 1.57 | 1.59 | 1.56 | 0.4575 | 0.3587 | 0.3251 |
| Right rear | 1.42 | 1.78 | 1.69 | 1.56 | 0.2767 | 0.8196 | 0.0322 |
| Left front end | 2.59 | 2.45 | 2.75 | 2.81 | 0.6336 | 0.0046 | 0.2145 |
| Right front end | 2.63 | 2.59 | 2.86 | 2.82 | 0.6403 | 0.0150 | 0.9540 |
| Left rear end | 2.27 | 2.33 | 2.55 | 2.53 | 0.8327 | 0.0074 | 0.6287 |
| Right rear end | 2.48 | 2.33 | 2.52 | 2.49 | 0.3155 | 0.2907 | 0.5563 |

[1]Values have been adjusted for covariate

Table T3 compares the somatic cell count (SCC) following a 30 day study of primiparous and multiparous cows for a commercially available teat dip that contains 0.5% iodine and 74% emollients (A) and a composition of the present invention comprising 0.5% iodine and 1.0% phospholipid with 0% added emollient (B). The treatment P value indicates that there in no statistical significance between the two products.

TABLE T3

(Effect of teat dip on somatic cell count)

| | Primiparous | | Multiparous | | P value | | |
|---|---|---|---|---|---|---|---|
| Item[1] | A | B | A | B | Treatment | Parity | *Parity |
| N | 23 | 25 | 45 | 43 | | | |
| SCC × 1000[a] | 79 | 123 | 250 | 355 | 0.3893 | 0.0200 | 0.7195 |
| N | 23 | 25 | 44 | 41 | | | |
| SCC × 1000[b] | 49 | 58 | 122 | 135 | 0.5947 | 0.0005 | 0.9220 |
| N | 23 | 25 | 44 | 41 | | | |
| SCC × 1000[c] | 52 | 62 | 126 | 138 | 0.6034 | 0.0004 | 0.9422 |

[1]Values have been adjusted for covariate
[a]All values used in analysis
[b]Values above 800,000 SCC removed
[c]Values above 998,000 SCC removed Table T4 lists the quantity and qualities of the milk obtained from a six week study of primiparous and multiparous cows for a commercially available teat dip that contains 1.0% iodine and 10% emollients (C), a composition of the present invention comprising 0.5% iodine and 1.0% phospholipid with 5% added emollient (D), and a composition of the present invention comprising 1.0% iodine and 1.0% phospholipid with 5% added emollient (E). The treatment P value indicates that the only statistical significance between the two products are the ECM (energy corrected milk), lactose, and SNF (solids not fat).

TABLE T4

(Effect of teat dip on milk yield and composition)

| | Primiparous | | | Multiparous | | | P value | | |
|---|---|---|---|---|---|---|---|---|---|
| Item[1] | C | D | E | C | D | E | T | P | T * P |
| N | 15 | 16 | 13 | 19 | 21 | 20 | | | |
| Milk, kg/day | 36.9 | 36.6 | 38.4 | 36.8 | 35.2 | 37.6 | 0.511 | 0.2032 | 0.6624 |
| ECM, kg/day | 37.3 | 37.5 | 38.7 | 36.2 | 35.6 | 38.0 | 0.0218 | 0.0655 | 0.7578 |
| Fat, % | 3.62 | 3.72 | 3.50 | 3.41 | 3.48 | 3.56 | 0.9815 | 0.0664 | 0.1756 |
| Protein, % | 3.15 | 3.10 | 3.15 | 3.14 | 3.17 | 3.15 | 0.0507 | 0.2834 | 0.1764 |
| Lactose, % | 4.99 | 4.93 | 4.99 | 4.90 | 4.93 | 4.93 | 0.0287 | 0.0148 | 0.1666 |
| SNF, % | 9.08 | 8.95 | 9.05 | 8.96 | 9.03 | 9.01 | 0.0047 | 0.4350 | 0.0246 |
| MUN, mg/dL | 17.61 | 16.66 | 17.27 | 16.75 | 16.72 | 17.31 | 0.1316 | 0.3325 | 0.2546 |
| Fat, kg/day | 1.31 | 1.35 | 1.33 | 1.23 | 1.25 | 1.33 | 0.0576 | 0.0780 | 0.4628 |
| Protein, kg/day | 1.15 | 1.13 | 1.20 | 1.14 | 1.10 | 1.78 | 0.2724 | 0.2675 | 0.9545 |
| Lactose, kg/day | 1.84 | 1.81 | 1.92 | 1.81 | 1.74 | 1.86 | 0.0915 | 0.1166 | 0.9228 |

[1]Values have been adjusted for covariate

Table T5 compares the somatic cell count (SCC) following a six week study of primiparous and multiparous cows for a commercially available teat dip that contains 1.0% iodine and 10% emollient (C), a composition of the present invention comprising 0.5% iodine and 1.0% phospholipid with 5% added emollient (D), and a composition of the present invention comprising 1.0% iodine and 1.0% phospholipid with 5% added emollient (E). The treatment P value indicates that there is no statistical difference between the two products.

TABLE T5

(Effect of teat dip on somatic cell count)

| Item[1] | Primiparous | | | Multiparous | | | P value | | |
|---|---|---|---|---|---|---|---|---|---|
| | C | D | E | C | D | E | T | P | T * P |
| N | 15 | 16 | 13 | 19 | 21 | 20 | | | |
| SCC × 1000[a] | 293 | 274 | 585 | 428 | 322 | 221 | 0.6659 | 0.5354 | 0.0911 |
| N | 15 | 16 | 13 | 19 | 21 | 20 | | | |
| SCC × 1000[b] | 115 | 74 | 124 | 215 | 168 | 139 | 0.4245 | 0.0196 | 0.4401 |
| N | 15 | 16 | 13 | 19 | 21 | 20 | | | |
| SCC × 1000[c] | 123 | 69 | 132 | 226 | 198 | 191 | 0.5851 | 0.0052 | 0.6955 |

[1]Covariate used for adjustment
[a]All values used in analysis - SCC2 × treat, SCC2 × parity, SCC2 × treat × parity interaction
[b]Values above 800,000 SCC removed - SCC2 × treat, SCC2 × treat × parity interaction
[c]Values above 998,000 SCC removed - SCC2 × treat, SCC2 × treat × parity interaction

EXAMPLES

Examples 1–6 describe formulas for a topical veterinary composition comprising an anti-microbial agent and a phospholipid-containing skin conditioner.

Generalized Ready-to-Use Teat Sanitizer:

A ready-to-use iodine teat sanitizer containing 1) a thickening agent such as an alkyl-hydroxy cellulose, 2) a synthetic surfactant such as an alkyl-aryl poly(ethoxy) ethanol or an n-alkyl poly(ethoxy) ethanol for detergency, wetting, and stability, 3) glycerin as an emollient, 4) a phosphate ester surfactant for added stability, 5) a phospholipid for enhanced teat conditioning, 6) an organic acid such as citric acid as a buffer, 7) a 20% iodine concentrate pre-manufactured by West Agro, and 8) a metal hydroxide for use as a pH neutralizer with the balance of ingredients being water. The solution is manufactured at ambient temperatures, blended until homogenous, and neutralized to a final pH between 4.8 and 5.2 for optimal free iodine:

a) where 2.00–35.00% is used of an alkyl-aryl poly (ethoxy) ethanol and/or an n-alkyl poly(ethoxy) ethanol where the alkyl moiety ranges from C7 to C14 and their degree of polymerization ranges from 7–14, with an ideal alkyl moiety of C8 or C9 and an ideal degree of polymerization of 9 or 10, b) where 0.00–0.50% is used of an alkyl-hydroxy cellulose with an alkyl moiety of C1 to C3, with an ideal alkyl moiety of C2, c) where 0.00–25.00% of glycerin is used, d) where 0.10–8.00% of an alkyl-aryl poly (ethoxy) phosphate ester is used where the alkyl moiety ranges from C7 to C14 and their degree of polymerization ranges from 2 to 6, with an ideal alkyl moiety of C8 or C9 and an ideal degree of polymerization of 4 to 6, and/or a C10 to a C18 fatty acid poly(ethoxy) phosphate ester including, but not limited to, capric, lauric, myristic, palmitic, stearic, oleic, linoleic, linolenic, and arachidonic acid and their corresponding isomers with a degree of polymerization ranging from 2 to 6, with a lauric phosphate ester as the ideal fatty acid with 3 degrees of polymerization, e) where 0.01–20% of a phospholipid is used where the fatty acid includes, but is not limited to, those acids whose carbon content ranges from C8 to C25 and preferably consists of at least one C—C double bond and no more than four C—C double bonds in their degree of unsaturation, with an ideal fatty acid carbon length of C18 and two C—C double bonds, or a natural oil such as coconut, olive, palm, or castor oil, or, any combination of a natural oil and an unsaturated fatty acid is preferred, f) where 0.50%–29.00% of an iodine concentrate such as TDC-20 provided by West Agro, Inc. which consists of at least a 20% iodine acid suspension, and g) where 0.00%–10.00% of a water soluble vitamin E (40% active) is used; however, 100% active vitamin E, or any bio-active tocopherol, may be substituted.

Example 1

Methocel J5MS (alkylhydroxy cellulose, 0.18 g) was added to warm water (70–75F, 87.64 g), and mixed until fully saturated. Igepal CO-720 (alkyl-aryl poly (ethoxy) ethanol, 3.00 g), glycerin (>99%, 5.00 g), linoleamidopropyl phosphatidylglycerol dimonium chloride phosphate, marketed under the trade name Arasilk EPA and Colalipid SAFL (1.00 g), CEDAPHOS FA-600 (phosphate ester, 0.50 g), and TDC-20 (20% iodine suspension, 2.5 g) are added and mixed with low shear until homogenous. Citric acid (0.05 g) is added and mixed thoroughly. The solution is neutralized to a pH of 4.8 to 5.2 with 50% sodium hydroxide (aq., 0.13 g). The solution in Example 1 is stable for at least one year at both ambient and elevated temperatures of 130 degrees Fahrenheit.

Example 2

Methocel J5MS (alkylhydroxy cellulose, 0.25 g) was added to warm water (70–75F, 90.58 g), and mixed until fully saturated. Igepal CO-720 (alkyl-aryl poly(ethoxy) ethanol, 3.00 g), glycerin (>99%, 1.99 g), linoleamidopropyl phosphatidylglycerol dimonium chloride phosphate, marketed under the trade name Arasilk EPA and Colalipid SAFL (1.00 g), CEDAPHOS FA-600 (phosphate ester, (0.50 g), and TDC-20 (20% iodine suspension, 2.5 g) are added and mixed with low shear until homogenous. Citric acid (0.05 g) is added and mixed thoroughly. The solution is neutralized to a pH of 4.8 to 5.2 with 50% sodium hydroxide (aq., 0.13 g). The solution in Example 2 is stable for at least one year at both ambient arid elevated temperatures of 130 degrees Fahrenheit.

Example 3

To ambient water (88.25 g), Iconol NP9 (alkylaryl poly (ethoxy) ethanol, 3.00 g, glycerin (>99%, 2.00 g), linoleamidopropyl phosphatidylglycerol dimonium chloride phosphate, marketed under the trade name Arasilk EFA and Colalipid SAFL (0.00 g), CEDAPHOS FA-600 (phosphate ester, 0.50 g), and TDC20 (20% iodine suspension, 5.0 g) are added and mixed with low shear until homogenous. Citric acid (0.05 g) is added and mixed thoroughly. The solution is neutralized to a pH of 4.8 to 5.2 with 50% sodium hydroxide (ag., 0.20 g). The solution in Example 3 is stable for at least one year at both ambient and elevated temperatures of 130 degrees Fahrenheit.

Example 4

To ambient water (85.25 g), Iconol NP9 (alkyl-aryl poly (ethoxy) ethanol, 3.00 g), glycerin (>99%, 5.00 g), linoleamidopropyl phosphatidylglycerol dimonium chloride phosphate, marketed under the trade name Arasilk EFA and Colalipid SAFL (1.00 g), CEDAPHOS FA-600 (phosphate ester, 0.50 g), and TDC-20 (20% iodine suspension, 5.0 g) are added and mixed with low shear until homogenous. Citric acid (0.05 g) is added and mixed thoroughly. The solution is neutralized to a pH of 4.8 to 5.2 with 50% sodium hydroxide (aq., 0.20 g). The solution in Example 4 is stable for at least one year at both ambient and elevated temperatures of 130 degrees Fahrenheit.

Generalized Teat Sanitizer Concentrate:

A concentrate of the general teat sanitizer is similarly prepared, except the amount of diluent (water) is reduced to provide a concentrate that when re-mixed with diluent prepares a ready-to-use product.

Example 5

Ambient water (1.00 g), Igepal CO-720 (alkyl-aryl poly (ethoxy) ethanol, 33.00 g), glycerin (>99%, 21.00 g), linoleamidopropyl phosphatidylglycerol dimonium chloride phosphate, marketed under the trade name Arasilk EFA and Colalipid SAFL (10.0 g), CEDAPHOS FA-600 (phosphate ester, 5.50 g), and TDC-20 (20% iodine suspension, 25.42 g) are all added together and mixed with low shear until homogenous. Citric acid (1.43 g) is added and mixed thoroughly. The solution is neutralized to a pH of 4.8 to 5.2 with 50% sodium hydroxide (aq., 2.65 g). The solution in Example 5 is stable for at least one year at both ambient and elevated temperatures of 130 degrees Fahrenheit. This concentrate is diluted 1 part concentrate to 10 parts water for a ready to use teat sanitizer.

Example 6

Ambient water (41.20 g), Iconol NP9 (alkyl-aryl poly (ethoxy) ethanol, 13.31 g), glycerin (>99%, 17.74 g), linoleamidopropyl phosphatidylglycerol dimonium chloride phosphate, marketed under the trade name Arasilk EFA and Colalipid SAFL (2.22 g), CEDAPHOS FA-600 (phosphate ester, 2.22 g), and TDC-20 (20% iodine suspension, 22.20 g) are all added together and mixed with low shear until homogenous. Citric acid (0.22 g) is added and mixed thoroughly. The solution is neutralized to a pH of 4.8 to 5.2 with 50% sodium hydroxide (aq., 0.89 g). The solution in Example 6 is stable for at least one year at both ambient and elevated temperatures of 130 degrees Fahrenheit. This concentrate is diluted 1 part concentrate to 3 parts water for a ready-to-use teat sanitizer.

Such preparations can be sterilized and, if desired, mixed with auxiliary agents, e.g., lubricants, preservatives, stabilizers, wetting agents, emulsifiers, salts for influencing osmotic pressure, buffers, coloring, preservatives and/or aromatic substances and the like which do not deleteriously react with the active compounds. Typical preservatives can include potassium sorbate, sodium metabisulfite, methyl paraben, propyl paraben, thimerosal, etc.

Indications to be Treated

Generally speaking, the compositions of the present invention comprise a therapeutically effective amount of an anti-microbial agent and a phospholipid-containing skin conditioner, employed to treat or prevent infection.

In one aspect, the invention provides a method to treat or prevent an infection caused by pathogens in or on the epidermal surface of the skin. In one embodiment, the infection is a mammary infection. In one alternative to this embodiment, the mammary infection is mastitis.

In another aspect, the invention provides a method to treat or prevent an infection caused by a fungus or virus in or on the epidermal surface of the skin.

The foregoing relates only to a limited number of embodiments that have been provided for illustration purposes only. It is intended that the scope of invention is defined by the appended claims and that modifications to the embodiments above may be made that do not depart from the scope of the invention.

What is claimed is:

1. A topical veterinary composition for the treatment of bovine mastitis comprising between about 0.1 and about 2 wt % iodine as an anti-microbial agent and a phospholipid-containing skin conditioner, wherein the phospholipid is selected from the group consisting of:

linoleamidopropyl phosphatidylglycerol dimonium chloride phosphate;

sunfloweramidopropyl phosphatidylglycerol dimonium chloride phosphate;

sodium olivamidopropyl phosphatidylglycerol dimonium chloride phosphate;

stearamidopropyl phosphatidylglycerol dimonium chloride phosphate;

ricinoleamidopropyl phosphatidylglycerol dimonium chloride phosphate;

di-linoleamidopropyl phosphatidylglycerol dimonium chloride phosphate;

poly (ethylene glycol) $_{=8}$ dimethicone sunfloweramidopropyl phosphatidylglycerol dimonium chloride phosphate complex;

dimethicone saffloweramidopropyl phosphatidylglycerol dimonium chloride phosphate complex;

sodium grapeseedamidopropyl phosphatidylglycerol dimonium chloride phosphate; and sodium borageamidopropyl phosphatidylglycerol dimonium chloride phosphate.

2. The composition of claim 1 comprising between about 0.01 and about 20 wt % phospholipid compound.

3. The composition of claim 1 further comprising a phosphate ester surfactant.

4. The composition of claim 3 wherein the phosphate ester surfactant comprises an alkyl-aryl poly (ethoxy) phosphate ester.

5. The composition of claim 4 wherein the phosphate ester surfactant has an alkyl moiety in the range of C7 to C14 and a degree of polymerization in the range of 2 to 6.

6. The composition of claim 3 wherein the phosphate ester surfactant comprises a C10 to a C18 fatty acid poly (ethoxy) phosphate ester.

7. The composition of claim 3 wherein the phosphate ester surfactant is selected from the group consisting of capric, lauric, myristic, palmitic, stearic, oleic, linoleic, linolenic, and arachidonic acid.

8. The composition of claim 1 further comprising a synthetic surfactant.

9. The composition of claim 8 wherein the synthetic surfactant comprises an alkyl-aryl poly (ethoxy) ethanol.

10. The composition of claim 9 wherein the synthetic surfactant has an alkyl moiety in the range of C7 to C14 and has a degree of polymerization in the range of 7–14.

11. The composition of claim 9 wherein the synthetic surfactant has an alkyl moiety in the range of C8 to C9 and has a degree of polymerization in the range of 9–10.

12. The composition of claim 8 wherein the synthetic surfactant comprises an n-alkyl poly (ethoxy) ethanol.

13. The composition of claim 12 wherein the synthetic surfactant has an alkyl moiety in the range of C7 to C14 and has a degree of polymerization in the range of 7–14.

14. The composition of claim 12 wherein the synthetic surfactant has an alkyl moiety in the range of C8 to C9 and has a degree of polymerization in the range of 9–10.

15. The composition of claim 1 further comprising a thickening agent.

16. The composition of claim 15 wherein the thickening agent comprises an alkyl-hydroxy cellulose.

17. The composition of claim 15 wherein the thickening agent has an alkyl moiety in the range of C1 to C3.

18. The composition of claim 15 wherein the thickening agent has an alkyl moiety of C2.

19. The composition of claim 1 further comprising any bioactive tocopherol.

20. The composition of claim 19 wherein the bioactive tocopherol is vitamin E.

21. The composition of claim 1 wherein the phospholipid is sunfloweramidopropyl phosphatidylglycerol dimonium chloride phosphate.

22. The composition of claim 1 wherein the phospholipid is sodium olivamidopropyl phosphatidylglycerol dimonium chloride phosphate.

23. The composition of claim 1 wherein the phospholipid is stearamidopropyl phosphatidylglycerol dimonium chloride phosphate.

24. The composition of claim 1 wherein the phospholipid is ricinoleamidopropyl phosphatidylglycerol dimonium chloride phosphate.

25. The composition of claim 1 wherein the phospholipid is di-linoleamidopropyl phosphatidylglycerol dimonium chloride phosphate.

26. The composition of claim 1 wherein the phospholipid is poly (ethylene glycol) $_{n=8}$ dimethicone sunfloweramidopropyl phosphatidylglycerol dimonium chloride phosphate complex.

27. The composition of claim 1 wherein the phospholipid is dimethicone saffloweramidopropyl phosphatidylglycerol dimonium chloride phosphate complex.

28. The composition of claim 1 wherein the phospholipid is sodium grapeseedamidopropyl phosphatidylglycerol dimonium chloride phosphate.

29. The composition of claim 1 wherein the phospholipid is sodium borageamidopropyl phosphatidylglycerol dimonium chloride phosphate.

30. A topical veterinary composition for the treatment of bovine mastitis wherein the composition is a concentrate for dilution with a diluent to yield a ready-to-use composition comprising between about 0.01 and about 20 wt % phospholipid compound and between about 0.1 and 2 wt % iodine and, wherein the phospholipid is selected from the group consisting of:

linoleamidopropyl phosphatidylglycerol dimonium chloride phosphate;

sunfloweramidopropyl phosphatidylglycerol dimonium chloride phosphate;

sodium olivamidopropyl phosphatidylglycerol dimonium chloride phosphate;

stearamidopropyl phosphatidylglycerol dimonium chloride phosphate;

ricinoleamidopropyl phosphatidylglycerol dimonium chloride phosphate;

di-linoleamidopropyl phosphatidylglycerol dimonium chloride phosphate;

poly (ethylene glycol) $_{n=8}$ dimethicone sunfloweramidopropyl phosphatidylglycerol dimonium chloride phosphate complex;

dimethicone saffloweramidopropyl phosphatidylglycerol dimonium chloride phosphate complex;

sodium grapeseedamidopropyl phosphatidylglycerol dimonium chloride phosphate; and sodium borageamidopropyl phosphatidylglycerol dimonium chloride phosphate.

31. A Topical veterinary composition for the treatment of bovine mastitis comprising between about 0.1 and about 2 wt % iodine as an anti-microbial agent and a phospholipid-containing skin conditioner, wherein the phospholipid is linoleamidopropyl phosphatidylglycerol dimonium chloride phosphate.

32. A topical veterinary composition for the treatment of bovine mastitis comprising iodine as an anti-microbial agent and a phospholipid-containing skin conditioner, wherein the phospholipid is selected from the group consisting of:

linoleamidopropyl phosphatidylglycerol dimonium chloride phosphate;

sunfloweramidopropyl phosphatidylglycerol dimonium chloride phosphate;

sodium olivamidopropyl phosphatidylglycerol dimonium chloride phosphate;

stearamidopropyl phosphatidylglycerol dimonium chloride phosphate;

ricinoleamidopropyl phosphatidylglycerol dimonium chloride phosphate;

di-linoleamidopropyl phosphatidylglycerol dimonium chloride phosphate;

poly (ethylene glycol) $_{n=8}$ dimethicone sunfloweramidopropyl phosphatidylglycerol dimonium chloride phosphate complex;

dimethicone saffloweramidopropyl phosphatidylglycerol dimonium chloride phosphate complex;

sodium grapeseedamidopropyl phosphatidylglycerol dimonium chloride phosphate; and sodium borageamidopropyl phosphatidylglycerol dimonium chloride phosphate, wherein the phospholipid is present in a weight ratio to iodine of between about 0.1:1 and about 10:1.

33. The composition of claim 32 wherein the phospholipid is present in a weight ratio to iodine of between about 1:1 and about 4:1.

34. The composition of claim 32 wherein the phospholipid is present in a weight ratio to iodine of between about 1.5:1 and about 2.5:1.

35. The composition of claim 32 wherein the phospholipid is present in a weight ratio to iodine of about 2:1.

* * * * *

UNITED STATES PATENT AND TRADEMARK OFFICE
CERTIFICATE OF CORRECTION

PATENT NO. : 7,182,948 B2 Page 1 of 1
APPLICATION NO. : 10/633945
DATED : February 27, 2007
INVENTOR(S) : Tyndall et al.

It is certified that error appears in the above-identified patent and that said Letters Patent is hereby corrected as shown below:

Column 14, claim 1, line 57: "(ethylene glycol) $_{=8}$" should read -- (ethylene glycol)$_{n=8}$ --.

Signed and Sealed this

Twenty-seventh Day of November, 2007

JON W. DUDAS
*Director of the United States Patent and Trademark Office*